(12) United States Patent
Kim

(10) Patent No.: US 9,978,136 B2
(45) Date of Patent: May 22, 2018

(54) MEDICINE PACKET INSPECTION APPARATUS AND METHOD

(71) Applicant: JVM CO., LTD., Daegu (KR)

(72) Inventor: Jun Ho Kim, Daegu (KR)

(73) Assignee: JVM CO., LTD., Daegu (KR)

( * ) Notice: Subject to any disclaimer, the term of this patent is extended or adjusted under 35 U.S.C. 154(b) by 0 days. days.

(21) Appl. No.: 15/189,784

(22) Filed: Jun. 22, 2016

(65) Prior Publication Data

US 2016/0379361 A1    Dec. 29, 2016

(30) Foreign Application Priority Data

Jun. 26, 2015 (KR) ........................ 10-2015-0091488

(51) Int. Cl.
| | |
|---|---|
| G06K 9/00 | (2006.01) |
| G06T 7/00 | (2017.01) |
| G01N 21/95 | (2006.01) |
| A61J 7/00 | (2006.01) |
| H04N 5/225 | (2006.01) |

(52) U.S. Cl.
CPC ............ G06T 7/0008 (2013.01); A61J 7/0076 (2013.01); G01N 21/95 (2013.01); G01N 21/9508 (2013.01); H04N 5/2256 (2013.01); *G06T 2207/30108* (2013.01)

(58) Field of Classification Search
CPC .................. G01N 21/9508; G06T 2207/30108
See application file for complete search history.

(56) References Cited

U.S. PATENT DOCUMENTS

| | | | | |
|---|---|---|---|---|
| 2013/0188038 A1* | 7/2013 | Tanimoto | ................. | A61J 3/06 348/86 |
| 2014/0347446 A1* | 11/2014 | Frandsen, Jr. | ........ | G06T 7/0004 348/46 |
| 2016/0114925 A1* | 4/2016 | Yuyama | ................ | G06T 7/0004 382/141 |
| 2017/0264867 A1* | 9/2017 | Amano | .................. | H04N 7/181 |

OTHER PUBLICATIONS

Murai et al "A Visual Inspection System for Prescription Drugs" IEEE, 2012 Fifth International Conference pp. 6. 2012.*

* cited by examiner

*Primary Examiner* — Oneal R Mistry
(74) *Attorney, Agent, or Firm* — Novick, Kim & Lee, PLLC; Jae Youn Kim

(57) ABSTRACT

A medicine packet inspection apparatus is provided. The medicine packet inspection apparatus includes a transfer unit configured to transfer medicine packets containing medicines, a photographing unit configured to photograph each medicine packet, a lighting unit configured to provide light to the medicine packet, and a controller configured to control the lighting unit to sequentially provide lights of different colors to the medicine packet and to control the photographing unit to photograph the medicine packet plural times corresponding to the lights of different colors.

12 Claims, 9 Drawing Sheets

MEDICINE PACKET INSPECTION APPARATUS AND METHOD

BACKGROUND OF THE INVENTION

Field of the Invention

The present invention relates to a medicine packet inspection apparatus and method and, more particularly, to a medicine packet inspection apparatus which sequentially provides lights of different colors and photographs a medicine packet plural times corresponding to the lights of different colors so as to raise accuracy in packet inspection and a medicine packet inspection method using the same.

Description of the Related Art

In general, medicine is given to a patient according to a prescription from a doctor in a hospital or a pharmacy.

Patients with a chronic disease periodically take the same medicine set over a long period of time. For example, a hypertensive patient or a diabetic patient should take the same medicine set every day for one month to three months or more. In this case, the patient is prescribed a large amount of medicines at once.

A unit of prescribed medicines, which should be taken at a time, is accommodated in a medicine packet, one side of which is opened. Thereafter, by sealing the opened side of the medicine packet, preparation of the medicine packet, in which medicines are packed, is completed.

Here, a plurality of medicine packets is continuously connected to form a medicine packet bundle. More specifically, a dose of medicine is automatically packed in a medicine packet and medicine packets are continuously connected, thus forming a medicine packet bundle.

In order to secure accuracy in medicines taken by a patient, operation to inspect whether or not some of prescribed medicines are omitted from a medicine packet, whether or not a medicine packet includes medicines which are not prescribed, whether or not a medicine packet includes a number of medicines exceeding the prescribed number of medicines, etc., is carried out.

Among methods of inspecting medicine packets, there is a method of photographing a medicine packet, detecting medicines from an acquired image, and judging whether or not the medicine packet is defective by comparing the detected medicines to medicine prescription information. Particularly, such a method may reduce a time taken to inspect medicine packets, if a large amount of medicines is prescribed at once, thus being widely used.

However, medicines have various colors. Therefore, if there is a medicine having a similar color to the color of the background of an acquired image, the medicine may not be precisely distinguished from the acquired image and thus judgment as to whether or not a medicine packet containing the medicines is defective may fail.

Further, if text is printed on a medicine packet and the text and medicines overlap, the medicines may not be precisely distinguished due to presence of the text and thus judgment as to whether or not a medicine packet containing the medicines is defective may fail.

SUMMARY OF THE INVENTION

Therefore, the present invention has been made in view of the above problems, and it is an object of the present invention to provide a medicine packet inspection apparatus which sequentially provides lights of different colors and photographs a medicine packet plural times corresponding to the lights of different colors so as to raise accuracy in packet inspection, and a medicine packet inspection method using the same.

In accordance with an aspect of the present invention, the above and other objects can be accomplished by the provision of a medicine packet inspection apparatus including a transfer unit configured to transfer medicine packets containing medicines, a photographing unit configured to photograph each medicine packet, a lighting unit configured to provide light to the medicine packet, and a controller configured to control the lighting unit to sequentially provide lights of different colors to the medicine packet and to control the photographing unit to photograph the medicine packet plural times corresponding to the lights of different colors.

The controller may judge whether or not medicines matching medicine prescription information are packed in the medicine packet using a plurality of images acquired by photographing the medicine packet under the lights of different colors.

The lighting unit may include a first light emitting element to emit light of a first color and a second light emitting element to emit light of a second color.

Here, the first color and the second color may be contrasting colors.

The controller may control the lighting unit to sequentially provide first light having the same color as the color of text printed on the surface of the medicine packet and at least one second light of a color different from the color of the first light.

The first light may have a color being the same as or complementary to the color of a medicine in the medicine packet.

The controller may judge whether or not medicines matching the medicine prescription information are packed in the medicine packet by detecting medicines from the respective images and combining the detected medicines.

Alternatively, the controller may judge whether or not medicines matching the medicine prescription information are packed in the medicine packet by combining the images and detecting medicines from an image acquired by combining the images.

The controller, if medicines matching the medicine prescription information are not packed in the medicine packet, may control the lighting unit to provide light of a different color from the colors of the lights of different colors, and control the photographing unit to additionally photograph the medicine packet corresponding to the light of a different color.

The lighting unit may be disposed opposite the photographing unit to provide light to the rear surface of the medicine packet.

The lighting unit may include a first light emitting unit disposed on the side surface of the photographing unit to provide light to the front surface of the medicine packet, a second light emitting unit disposed on the side surface of the medicine packet, and a third light emitting unit disposed opposite the photographing unit to provide light to the rear surface of the medicine packet.

In accordance with another aspect of the present invention, there is provided a medicine packet inspection method including transferring medicine packets containing medicines, sequentially providing lights of different colors to each medicine packet, and photographing the medicine packet plural times corresponding to the lights of different colors.

The medicine packet inspection method may further include judging whether or not medicines matching medicine prescription information are packed in the medicine packet using a plurality of images acquired by photographing the medicine packet under the lights of different colors.

In sequential provision of the lights of different colors, first light having the same color as the color of text printed on the surface of the medicine packet and at least one second light of a color different from the color of the first light may be sequentially emitted.

In judgment, whether or not medicines matching the medicine prescription information are packed in the medicine packet may be judged by detecting medicines from the respective images and combining the detected medicines.

In judgment, whether or not medicines matching the medicine prescription information are packed in the medicine packet may be judged by combining the images and detecting medicines from an image acquired by combining the images.

The medicine packet inspection method may further include, if medicines matching the medicine prescription information are not packed in the medicine packet, providing light of a different color from the colors of the lights of different colors, and additionally photographing the medicine packet corresponding to the light of a different color.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, one embodiment of the present invention will be described in detail with reference to the accompanying drawings.

Figure 1:
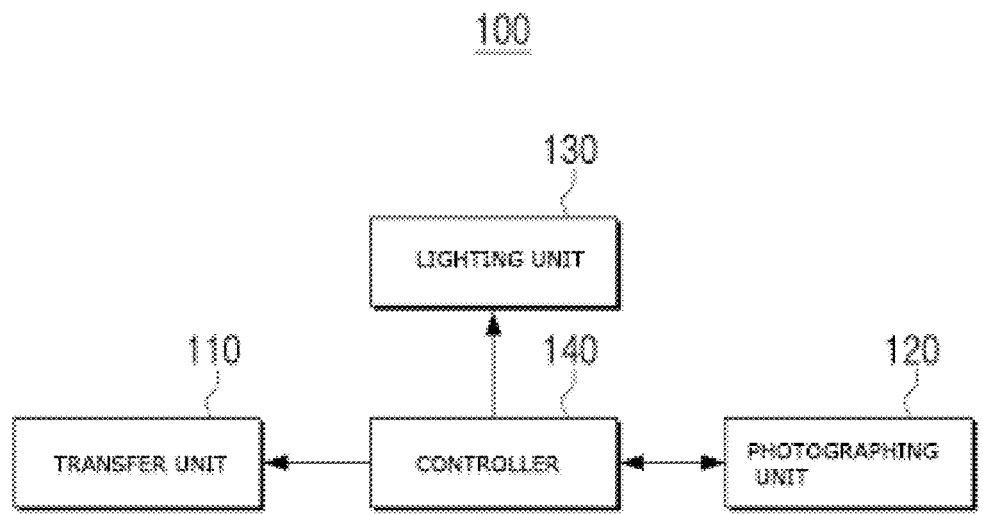
FIG. 1 is a block diagram illustrating the configuration of a medicine packet inspection apparatus in accordance with one embodiment of the present invention.

FIG. 1 is a block diagram illustrating the configuration of a medicine packet inspection apparatus in accordance with one embodiment of the present invention.

With reference to FIG. 1, a medicine packet inspection apparatus 100 includes a transfer unit 110, a photographing unit 120, a lighting unit 130, and a controller 140.

The transfer unit 110 transfers medicine packets in which medicines are packed. More specifically, in order to inspect the medicine packets in which medicines are packed, the transfer unit 110 may transfer a medicine packet bundle, in which the medicine packets are continuously connected, to the photographing unit 120.

Further, the transfer unit 110 may sequentially locate the medicine packets at the photographing unit 120 one by one. More specifically, the transfer unit 110 may locate one medicine packet of the medicine packet bundle at the photographing unit 120 so that the medicine packet is inspected, and stop transfer of the medicine packet bundle during inspection. After inspection, the transfer unit 110 may transfer the medicine packet bundle so that the next medicine packet is located at the photographing unit 120.

The photographing unit 120 photographs the medicine packet. More specifically, the photographing unit 120 may photograph the medicine packet transferred to the photographing unit 120 by the transfer unit 110 and thus acquire images to detect the number and kinds of medicines packed in the medicine packet.

The photographing unit 120 photographs the medicine packet plural times corresponding to lights of different colors under the control of the controller 140. More specifically, when the lighting unit 130 sequentially provides a plurality of lights of different colors to the medicine packet, the photographing unit 120 may photograph the medicine packet plural times corresponding to the lights of different colors.

For example, the photographing unit 120 may photograph the medicine packet plural times corresponding to lights of different colors in a manner, in which the photographing unit 120 executes first photographing when the lighting unit 130 provides first light, executes second photographing when the lighting unit 130 provides second light of a different color from the first light, and executes third photographing when the lighting unit 130 provides third light of a different color from the first and second lights.

The lighting unit 130 provides light to the medicine packet. More specifically, the lighting unit 130 may be implemented as a backlight or light emitting elements having a predetermined shape. For example, if the lighting unit 130 is implemented as a backlight, the backlight may be disposed at a position opposing the position of the photographing unit 120. For example, as exemplarily shown in FIGS. 2 to 3B, if the photographing unit 120 is disposed on the front surface of the medicine packet, the lighting unit 130 may be disposed on the rear surface of the medicine packet. In this case, the lighting unit 130 may emit light from the rear end of the medicine packet toward the photographing unit 120. Such a disposition shape will be described later with reference to FIGS. 2 to 3B.

The lighting unit 120 may be implemented as general light emitting elements as well as the above-described backlight, or be implemented as a structure in which the backlight and the light emitting elements are combined. Such a case will be described later with reference to FIGS. 4A to 4D.

The lighting unit 130 provides lights of different colors to the medicine packet under the control of the controller 140. For example, the lighting unit 130 may provide a plurality of lights of different colors to the medicine packet in a manner in which the lighting unit 130 provides first light, provides second light of a different color from the first light after provision of the first light, and provides third light of a different color from the first and second lights after provision of the second light. Here, the different colors may be contrasting colors, and at least one of the different colors may be the same as the color of the medicine or be complementary to the color of the medicine.

The lighting unit 130 may be implemented as a plurality of light emitting elements. If the lighting unit 130 is implemented as light emitting elements, the lighting unit 130 may include a first light emitting element to emit light of a first color and a second light emitting element to emit light of a second color. For example, the lighting unit 130 may include a light emitting element to emit red light and a light emitting element to emit blue light. Here, the light emitting elements may be elements to emit light of a specific color, i.e., various types of elements including an incandescent light, a fluorescent light, a CCFL, an LED, an OLED, an AMOLED, etc.

Further, although this embodiment describes the light emitting unit 130 as including two kinds of light emitting elements, the light emitting unit 130 is not limited thereto. For example, the lighting unit 130 may include a first light emitting element to emit light of a first color, a second light emitting element to emit light of a second color, a third light emitting element to emit light of a third color, a fourth light emitting element to emit light of a fourth color, and a fifth light emitting element to emit light of a fifth color.

If the lighting unit 130 is implemented as light emitting elements, one light emitting element corresponding to each color may be used or a plurality of light emitting elements corresponding to each color may be used. For example, the lighting unit 130 may include a plurality of light emitting elements to emit light of a first color and a plurality of light emitting elements to emit light of a second color. Although this embodiment describes that light emitting elements, each of which emits light of one color, one light emitting element may form the lighting unit 130 if the light emitting element may emit light of a plurality of colors.

The controller 140 controls the lighting unit 130 to sequentially provide lights of different colors to the medicine packet. For example, the controller 140 may control the lighting unit 130 to sequentially provide lights of different colors to the medicine packet in a manner in which the lighting unit 130 provides first light, provides second light of a different color from the first light after provision of the first light, and provides third light of a different color from the first and second lights after provision of the second light.

Further, the controller 140 controls the photographing unit 120 to photograph the medicine packet plural times corresponding to a plurality of lights of different colors. More specifically, when the lighting unit 130 sequentially provides a plurality of lights of different colors to the medicine, the controller 140 may control the photographing unit 120 to photograph the medicine packet plural times corresponding to the lights of different colors.

The controller 140 may judge whether or not medicines matching medicine prescription information are packed in the medicine packet using a plurality of images acquired by photographing the medicine packet under the lights of different colors.

More specifically, the controller 140 may receive the images acquired by photographing the medicine packet from the photographing unit 120, detect the kinds and number of the medicines from the received images, and judge whether or not medicines matching medicine prescription information are packed in the medicine packet by comparing the detected kinds and number of the medicines with the medicine prescription information.

Further, the controller 140 may control the lighting unit 130 to sequentially emit first light having the same color as the color of text printed on the surface of the medicine packet and second light of a color different from the color of the first light.

For example, if the color of the text printed on the surface of the medicine packet is black, the controller 140 may control the lighting unit 130 to emit black light and then to emit light of at least one color differing from black after emission of black light.

In this case, when a user pre-inputs the color of the text printed on the surface of the medicine packet using an input unit (not shown) of the medicine packet inspection apparatus 100, the controller 140 may control the lighting unit 130 to emit light of the pre-input color.

Further, the medicine packet inspection apparatus 100 may include a sensor unit (not shown). The sensor unit (not shown) may detect the color of the text printed on the surface of the medicine packet, and the controller 140 may control the lighting unit 130 to emit light having the same color as the detected color of the text.

The controller 140 may detect medicines from the respective acquired images and judge whether or not medicines matching the medicine prescription information are packed in the medicine packet by combining the detected medicines.

More specifically, the controller 140 may detect medicines packed in the medicine packet from each of the acquired respective images. Further, if a specific medicine is not detected from a first image and the specific medicine is detected from a second image, the controller 140 may combine a result of detection from the first image and a result of detection from the second image and thus judge that the specific medicine is present in the medicine packet.

For example, if a first medicine, a second medicine, and a fourth medicine are detected from the first image and the first medicine, the second medicine, a third medicine and a fifth medicine are detected from the second image acquired using light of a different color from the color of light for the first image, the controller 140 may judge that the first medicine, the second medicine, the third medicine, the fourth medicine and the fifth medicine are present in the medicine packet.

In this case, if the medicine prescription information includes the first medicine, the second medicine, the third medicine, the fourth medicine and the fifth medicine, the controller 140 may judge that medicines matching the medicine prescription information are packed in the medicine packet.

The controller 140 may combine a plurality of images, detect medicines from an image acquired by combining the images, and judge whether or not medicines matching the medicine prescription information are packed in the medicine packet.

For example, the controller 140 may generate a third image by combining the first image in which the first medicine, the second medicine and the fourth medicine are distinguished, and the second image in which the first medicine, the second medicine, the third medicine and the fifth medicine are distinguished. Then, the controller 140 may detect the first medicine, the second medicine, the third medicine, the fourth medicine and the fifth medicine from the third image.

Therefore, the controller 140 may judge that the first medicine, the second medicine, the third medicine, the fourth medicine and the fifth medicine are present in the medicine packet.

In this case, if the medicine prescription information includes the first medicine, the second medicine, the third medicine, the fourth medicine and the fifth medicine, the controller 140 may judge that medicines matching the medicine prescription information are packed in the medicine packet.

If any medicines matching the medicine prescription information are not packed in the medicine packet, the controller 140 may control the lighting unit 130 to provide light of a color differing from the lights of different colors. For example, if, as a result of photographing the medicine packet using first light of a first color, second light of a second color and third light of a third color and comparing the photographed images with the medicine prescription information, it is judged that medicines in the medicine packet do not coincide with the medicine prescription information, the controller 140 may control the lighting unit 130 to provide fourth light of a fourth color and fifth light of a fifth color.

In this case, the controller 140 may control the photographing unit 120 to additionally photograph the medicine packet corresponding to the lights of different colors. For example, corresponding to provision of the fourth light of the fourth color and the fifth light of the fifth color by the lighting unit 130, the controller 140 may control the photographing unit 120 to execute fourth photographing and fifth photographing of the medicine packet.

Thereby, the number of frequency of providing light and the number of frequency of photographing are limited and thus a time taken for medicine packet inspection may be reduced in a general inspection process, and additional inspection is executed if a result of inspection does not coincide with medicine prescription information, thereby improving accuracy in inspection.

Meanwhile, the controller 140 may be also referred to as a "processor".

Further, the controller 140 may control the overall operation of the medicine packet inspection apparatus 100.

Figure 2:
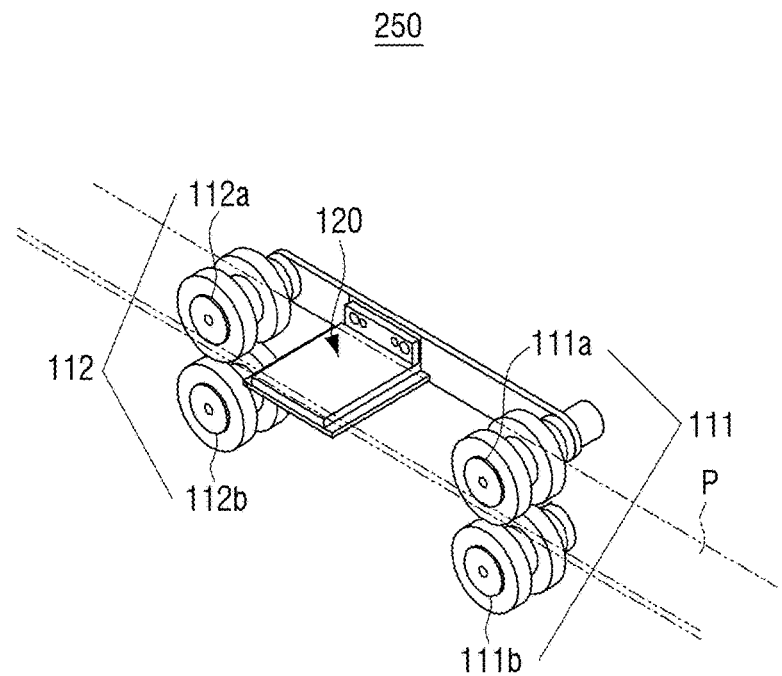
FIG. 2 is a perspective view illustrating a transfer unit and a photographing unit of an inspection unit in accordance with one embodiment of the present invention.

FIG. 2 is a perspective view illustrating the transfer unit 110 and the photographing unit 120 of an inspection unit 250 in accordance with one embodiment of the present invention.

With reference to FIG. 2, the transfer unit 110 may include entrance rollers 111 and exit rollers 112.

A medicine packet bundle P in which medicine packets are continuously connected enters the photographing unit 120 by rotation of the entrance rollers 111 and exits the photographing unit 120 by rotation of the exit rollers 112.

More specifically, the entrance rollers 111 may include an upper entrance roller 111*a* contacting the upper part of a medicine packet and a lower entrance roller 111*b* contacting the lower part of the medicine packet, and the medicine packet bundle P may enter the photographing unit 120 by rotation of the upper entrance roller 111*a* and the lower entrance roller 111*b*.

The exit rollers 112 may include an upper exit roller 112*a* contacting the upper part of a medicine packet and a lower exit roller 112*b* contacting the lower part of the medicine packet, the medicine packet bundle P may exit the photographing unit 120 by rotating the upper exit roller 112*a* and the lower exit roller 112*b*.

When the medicine packet enters the photographing unit 120, operation of the entrance rollers 111 and the exit rollers 112 is stopped so as to photograph the medicine packet and, when the photographing unit 120 finishes photographing of the medicine packet, the entrance rollers 111 and the exit rollers 112 start to operate so that a medicine packet located at the next position of the photographed medicine packet is located at the photographing unit 120.

The photographing unit 120 is disposed between the entrance rollers 111 and the exit rollers 112. The photographing unit 120 is located under the medicine packet bundle P and may thus photograph the medicine packet.

Since the width and length of the photographing unit 120 correspond to the width and length of the medicine packet, the photographing unit 120 may photograph medicine packets one by one. However, the disclosure of the present invention is not limited thereto and the photographing unit 120 may be implemented to have a sufficient size to simultaneously photograph two or more medicine packets.

Figure 3A:
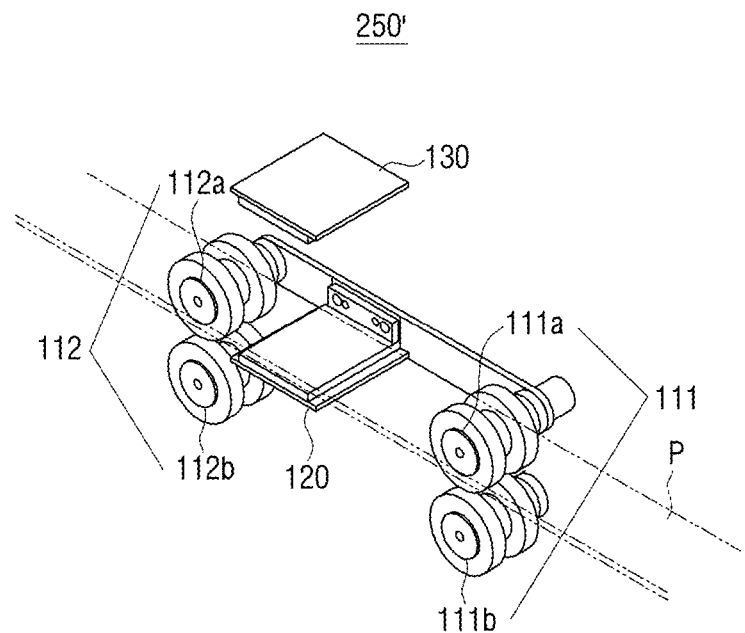
FIG. 3A is a perspective view illustrating a transfer unit, a photographing unit and a lighting unit of a medicine packet inspection apparatus in accordance with one embodiment of the present invention.

FIG. 3A is a perspective view illustrating a transfer unit 110, a photographing unit 120 and a lighting unit 130 of a medicine packet inspection apparatus 250' in accordance with one embodiment of the present invention.

With reference to FIG. 3A, the lighting unit 130 may be disposed opposite the photographing unit 120. For example, as exemplarily shown in FIG. 3A, the photographing unit 120 may be located under the medicine packet bundle P and the lighting unit 130 may be located at the opposite side of the medicine packet bundle P. That is, the lighting unit 130 may be located at a position on the medicine packet bundle P corresponding to the photographing unit 120.

Although this embodiment describes that the medicine packet bundle P is placed in parallel with the ground, the photographing unit 120 is disposed at the lower end of a medicine packet and the lighting unit 130 is located at the upper end of the medicine packet, the disclosure of the present invention is not limited thereto. For example, the medicine packet bundle P may be placed vertical to the ground, the photographing unit 120 may be located at the left side of a medicine packet and the lighting unit 130 may be located at the right side of the medicine packet.

Further, although this embodiment describes that the photographing unit 120 is disposed at the lower end of a medicine packet and the lighting unit 130 is disposed at the upper end of the medicine packet, the disclosure of the present invention is not limited thereto. For example, the photographing unit 120 may be disposed at the upper end of a medicine packet and the lighting unit 130 may be disposed at the lower end of the medicine packet.

The lighting unit 130 may have a width and a length corresponding to the width and length of the photographing unit 120. Further, the lighting unit 130 may provide light in a direction toward the medicine packet and the photographing unit 120. Therefore, the lighting unit 130 may uniformly provide light throughout an area photographed by the photographing unit 120.

Figure 3B:
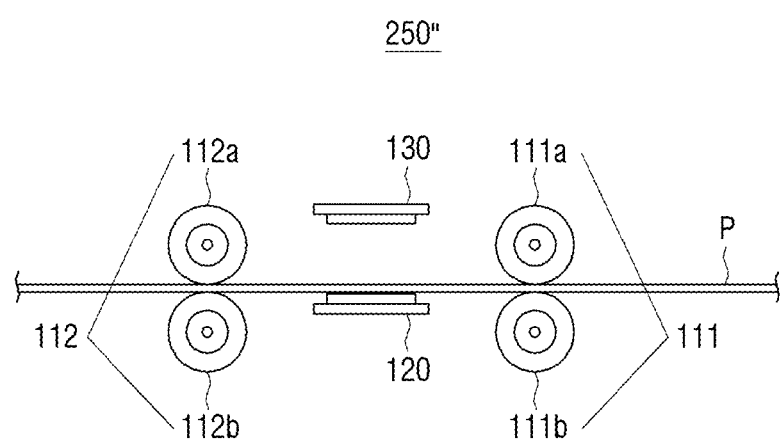
FIG. 3B is a front view illustrating a transfer unit, a photographing unit and a lighting unit of a medicine packet inspection apparatus in accordance with another embodiment of the present invention.

FIG. 3B is a front view illustrating a transfer unit 110, a photographing unit 120 and a lighting unit 130 of a medicine packet inspection apparatus 250" in accordance with another embodiment of the present invention.

With reference to FIG. 3, the lighting unit 130 and the photographing unit 20 face each other across from a medicine packet photographed by the photographing unit 120.

Figure 4A:
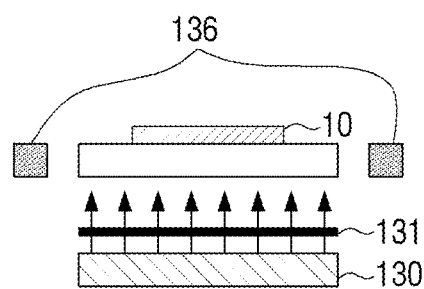
FIGS. 4A to 4D are views illustrating disposition types of a transfer unit, a photographing unit and a lighting unit in accordance with other embodiments of the present invention.
Figure 4B:
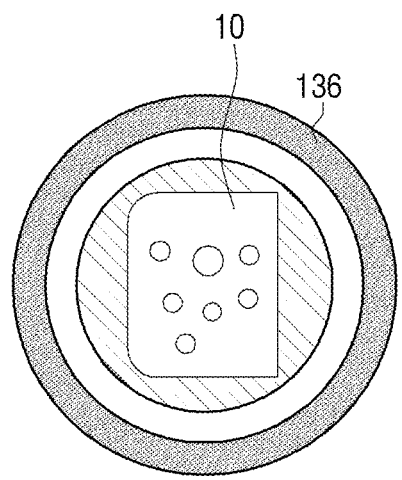
Figure 4C:
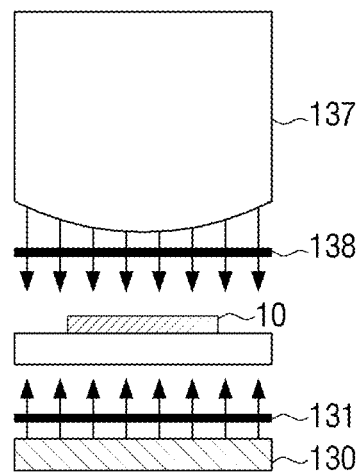
Figure 4D:
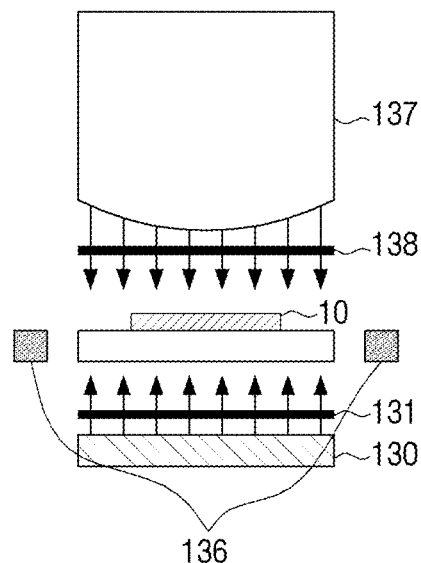

FIGS. 4A to 4D are views illustrating shapes of lighting units in accordance with other embodiments of the present invention. More specifically, FIG. 4A is a view illustrating a lighting unit to which a ring-shaped subsidiary lighting unit is added, FIG. 4B is a top view of the lighting unit of FIG. 4A, FIG. 4C is a view illustrating a lighting unit to which a subsidiary lighting unit disposed in the opposite direction of the lighting unit is added, and FIG. 4D is a view illustrating a lighting unit to which both subsidiary lighting units shown in FIGS. 4A and 4C are added. With reference to FIGS. 4A and 4B, the lighting unit 130 may emit light from an area below a medicine packet 10 in a direction toward the medicine packet 10. Here, in order to uniformly emit light to the medicine packet 10, a first polarizing member 131 may be disposed between the lighting unit 130 and the medicine packet 10. Although the above-described embodiments illustrate the lighting unit 130 as being disposed under the medicine packet 10, the lighting unit 130 may be disposed on the medicine packet 10 in implementation.

A first subsidiary lighting unit 136 may be a ring-shaped light element, which is disposed around the medicine packet 10, and emit light in the direction toward the medicine packet 10. Further, in implementation, a polarizing member may be disposed between the first subsidiary lighting unit 136 and the medicine packet 10.

In implementation, the first subsidiary lighting unit 136 may emit light having the same color as light from the lighting unit 130 while interworking with the lighting unit 130, or emit light of a different color as light from the lighting unit 130. For example, if the lighting unit 130 is capable of emitting green light and the first subsidiary lighting unit 136 is capable of emitting red light, the controller 140 may control the lighting unit 130 alone to emit light when green light is required, and control the first subsidiary lighting unit 136 alone to emit light when red light is required. Further, the controller 140 may control the lighting unit 130 to emit green light and control the first subsidiary light unit 136 to emit red light when yellow light is required, thereby allowing yellow light to be emitted to the medicine packet 10 by mixing of green light and red light.

With reference to FIG. 4C, the lighting unit 130 emits light from an area below the medicine packet 10 in the direction toward the medicine packet 10. Here, the first polarizing member 131 may be disposed between the lighting unit 130 and the medicine packet 10 so as to uniformly irradiate the medicine packet with light. Although the embodiment describes the lighting unit 130 as being disposed under the medicine packet, the medicine packet may be disposed on the medicine packet in implementation.

A second subsidiary lighting unit 137 emits light from an area above the medicine packet 10 toward the medicine packet 10. Here, the second subsidiary lighting unit 137 may have a dome shape so as to uniformly irradiate the medicine packet 10 with light. Further, in order to uniformly disperse light, a second polarizing member 138 may be disposed between the second subsidiary lighting unit 137 and the medicine packet 10.

In implementation, the second subsidiary lighting unit 137 may emit light having the same color as light from the lighting unit 130 while interworking with the lighting unit 130, or emit light of a different color as light from the lighting unit 130.

With reference to FIG. 4D, the lighting unit 130 emits light from an area below the medicine packet 10 in the direction toward the medicine packet 10.

The first subsidiary lighting unit 136 may be a ring-shaped light element, which is disposed around the medicine packet 10, and emit light in the direction toward the medicine packet 10.

The second subsidiary lighting unit 137 emits light from an area above the medicine packet 10 in a direction toward the medicine packet.

If the lighting unit 130, the first subsidiary lighting unit 136 and the second subsidiary lighting unit 137 emit lights to the medicine packet 10, three lighting units 130, 136 and 137 may emit lights having the same color or individually emit lights of different colors. Further, the lighting unit 130, the first subsidiary lighting unit 136 and the second subsidiary lighting unit 137 may simultaneously emit lights of different colors (for example, green light, red light and blue light) and thus irradiate the medicine packet 10 with light of a different color (white light) through light mixing.

Although the above embodiment describes two subsidiary lighting units as being additionally used, three or more subsidiary lighting units may be additionally used in actual implementation.

Figure 5A:
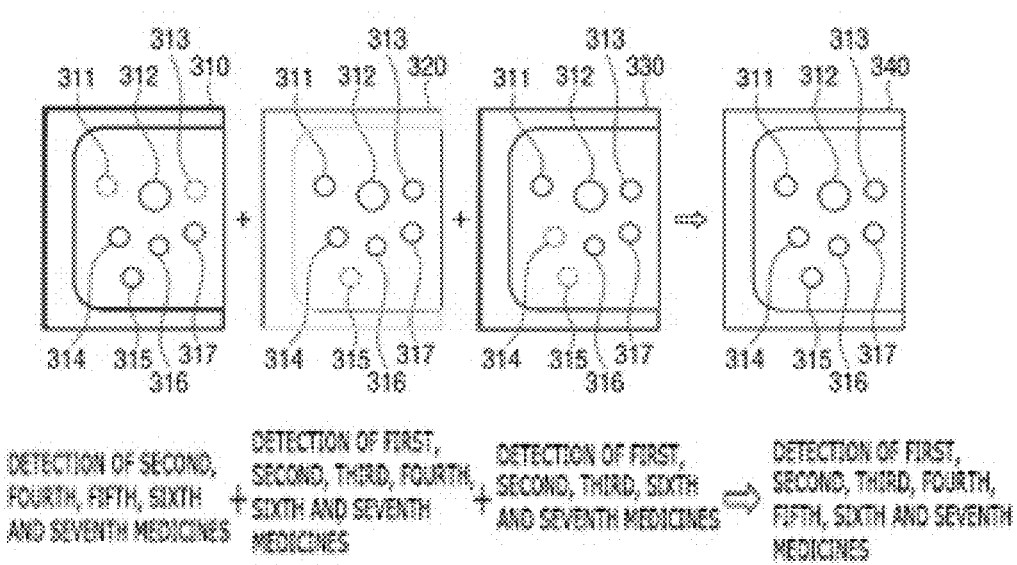
FIGS. 5A and 5B are views, each of which illustrates a process of inspecting a medicine packet using a plurality of images in accordance with one embodiment of the present invention.
Figure 5B:
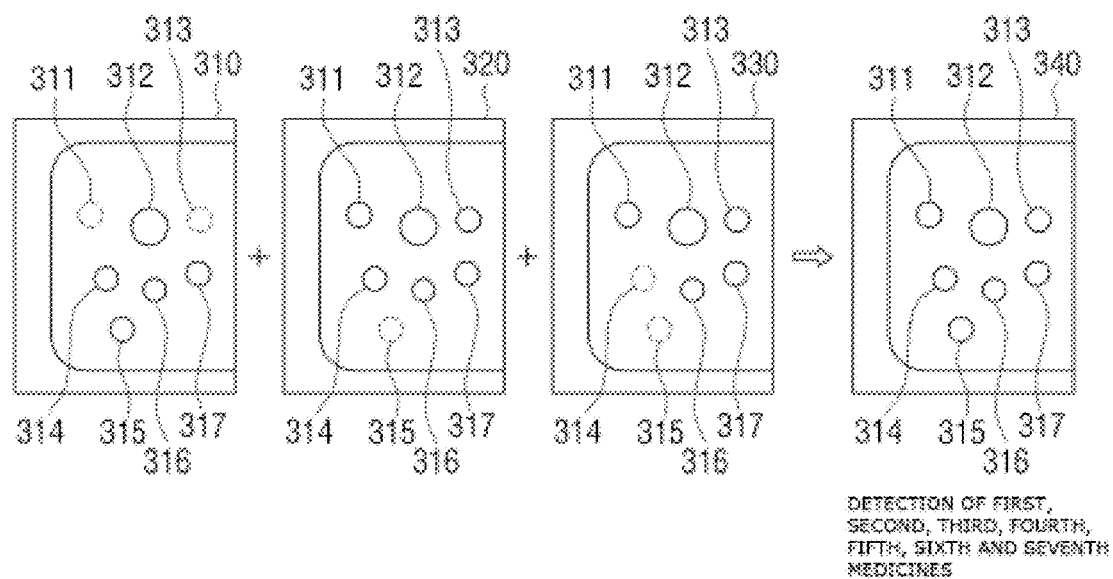

FIGS. 5A and 5B are views, each of which illustrates a process of inspecting a medicine packet using a plurality of images in accordance with one embodiment of the present invention.

FIG. 5A illustrates a method of judging whether or not medicines matching medicine prescription information are packed in a medicine packet by detecting medicines from each of a plurality of images and combining the detected medicines.

FIG. 5A shows a plurality of images 310, 320 and 330 acquired by photographing a medicine packet, in which a first medicine 311, a second medicine 312, a third medicine 313, a fourth medicine 314, a fourth medicine 315, a sixth medicine 316 and a seventh medicine 317 are packed, under lights of different colors three times.

In this case, the controller 140 may detect medicines packed in the medicine packet from the photographed images 310, 320 and 330.

Medicines which are detected by the controller 140 are shown by a solid line, and medicines which are not detected by the controller 140 are shown by a dotted line.

The second medicine 312, the fourth medicine 314, the fifth medicine 315, the sixth medicine 316 and the seventh medicine 317 are detected from the first image 310, but the first medicine 311 and the third medicine 313 are not detected from the first image 310.

The first medicine 311, the second medicine 312, the third medicine 313, the fourth medicine 314, the sixth medicine 316 and the seventh medicine 317 are detected from the second image 320, but the fifth medicine 315 is not detected from the second image 320.

The first medicine 311, the second medicine 312, the third medicine 313, the sixth medicine 316 and the seventh medicine 317 are detected from the third image 330, but the fourth medicine 314 and the fifth medicine 315 are not detected from the third image 330.

In this case, the controller 140 may judge whether or not medicines matching medicine prescription information are packed in the medicine packet by combining results of detection of the medicines from the three images 310, 320 and 330.

That is, since the first medicine 311 is detected from the second image 320 and the third image 330, the controller 140 may judge that the first medicine 311 is present in the medicine packet.

Since the second medicine 312 is detected from the first image 310, the second image 320 and the third image 330, the controller 140 may judge that the second medicine 311 is present in the medicine packet.

Since the fifth medicine 315 is detected from the first image 310, the controller 140 may judge that the fifth medicine 315 is present in the medicine packet.

By repeating such a process in the case of the third medicine 313, the fourth medicine 314, the sixth medicine 316 and the seventh medicine 317, the controller 140 may judge that the first medicine 311, the second medicine 312, the third medicine 313, the fourth medicine 314, the fifth medicine 315, the sixth medicine 316 and the seventh medicine 317 are present in the medicine packet.

In this case, if the medicine prescription information includes the first medicine 311, the second medicine 312, the third medicine 313, the fourth medicine 314, the fifth medicine 315, the sixth medicine 316 and the seventh medicine 317, the controller 140 may judge that medicines matching the medicine prescription information are packed in the medicine packet.

In such a manner, if a specific medicine is detected from an arbitrary image among a plurality of images, it may be judged that the detected specific medicine is present in the medicine packet.

FIG. 5B illustrates a method of judging whether or not medicines matching medicine prescription information are packed in a medicine packet by combining a plurality of images and detecting medicines from an image acquired by combining the images.

FIG. 5B shows a plurality of images 310, 320 and 330 acquired by photographing a medicine packet, in which a first medicine 311, a second medicine 312, a third medicine 313, a fourth medicine 314, a fifth medicine 315, a sixth medicine 316 and a seventh medicine 317 are packed, under lights of different colors three times.

In each image, medicines which are clearly displayed so as to be detectable are shown by a solid line, and medicines which are not clearly displayed are shown by a dotted line.

In the first image 310, the second medicine 312, the fourth medicine 314, the fifth medicine 315, the sixth medicine 316 and the seventh medicine 317 are clearly displayed so as to be detectable, but the first medicine 311 and the third medicine 313 are not clearly displayed so as to be undetectable.

In the second image 320, the first medicine 311, the second medicine 312, the third medicine 313, the fourth medicine 314, the sixth medicine 316 and the seventh medicine 317 are clearly displayed so as to be detectable, but the fifth medicine 315 is not clearly displayed so as to be undetectable.

In the third image 330, the first medicine 311, the second medicine 312, the third medicine 313, the sixth medicine 316 and the seventh medicine 317 are clearly displayed so as to be detectable, but the fourth medicine 314 and the fifth medicine 315 are not clearly displayed so as to be undetectable.

In this case, the controller 140 may generate a new image 340 by combining the photographed images 310, 320 and 330.

In the image 340 acquired by combining the images 310, 320 and 330, the first medicine 311, the second medicine 312, the third medicine 313, the fourth medicine 314, the fifth medicine 315, the sixth medicine 316 and the seventh medicine 317 are clearly displayed so as to be detectable.

The controller 140 may judge whether or not medicines matching medicine prescription information are packed in the medicine packet by detecting medicines from the new image 340 acquired by combining the images 310, 320 and 330.

That is, since the first medicine 311, the second medicine 312, the third medicine 313, the fourth medicine 314, the fifth medicine 315, the sixth medicine 316 and the seventh medicine 317 are detected from the image 340, the controller 140 may judge that the first medicine 311, the second medicine 312, the third medicine 313, the fourth medicine 314, the fifth medicine 315, the sixth medicine 316 and the seventh medicine 317 are present in the medicine packet.

In this case, if the medicine prescription information includes the first medicine 311, the second medicine 312, the third medicine 313, the fourth medicine 314, the fifth medicine 315, the sixth medicine 316 and the seventh medicine 317, the controller 140 may judge that medicines matching the medicine prescription information are packed in the medicine packet.

Figure 6:
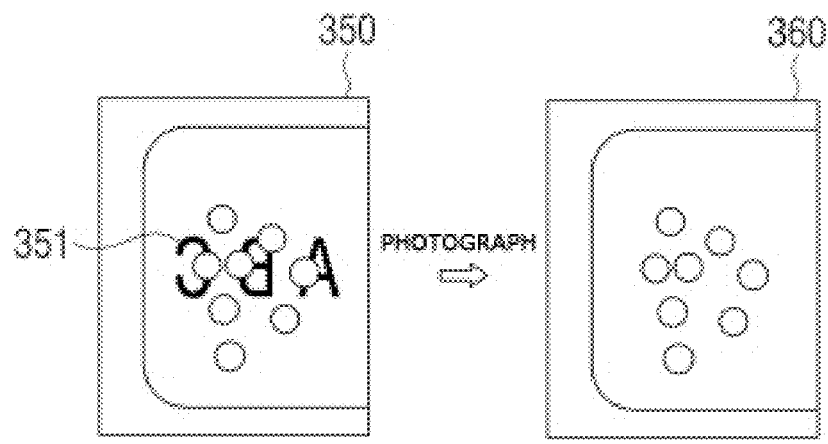
FIG. 6 is a view illustrating photographing of a medicine packet by providing light having the same color as the color of text in accordance with one embodiment of the present invention.

FIG. 6 is a view illustrating photographing of a medicine packet by providing light having the same color as the color of text in accordance with one embodiment of the present invention.

With reference to FIG. 6, a medicine packet 350 contains a plurality of medicines. Further, text 351 "ABC" is printed on the surface of the medicine packet 350.

If the medicine packet 350 is photographed under the condition that medicines in the medicine packet 350 overlap the text 351 printed on the medicine packet 350, the outlines of the medicines are not properly detected and, consequently, medicine recognition may fail.

Therefore, if the medicine packet 350 is photographed using light of a color which is the same as or similar to the color of the text 351 printed on the medicine packet 350 as a background color, an image 360 from which the text 351 is removed may be acquired.

The controller 140 may control the lighting unit 130 to sequentially emit first light having the same color as the color of the text printed on a medicine packet and at least one second light of a color different from the color of the first light.

For example, when the color of the text is black, the controller 140 may control the lighting unit 130 to emit first light of black.

After emission of the first light from the lighting unit 130, the controller 140 may control the lighting unit 130 to emit light of colors other than black. For example, the lighting unit 130 emits black light and then emits red light.

The second light may have one or more colors. For example, the lighting unit 130 may emit black light having the same color as the text, emit red light after emission of black light and then emit blue light after emission of red light.

Figure 7:
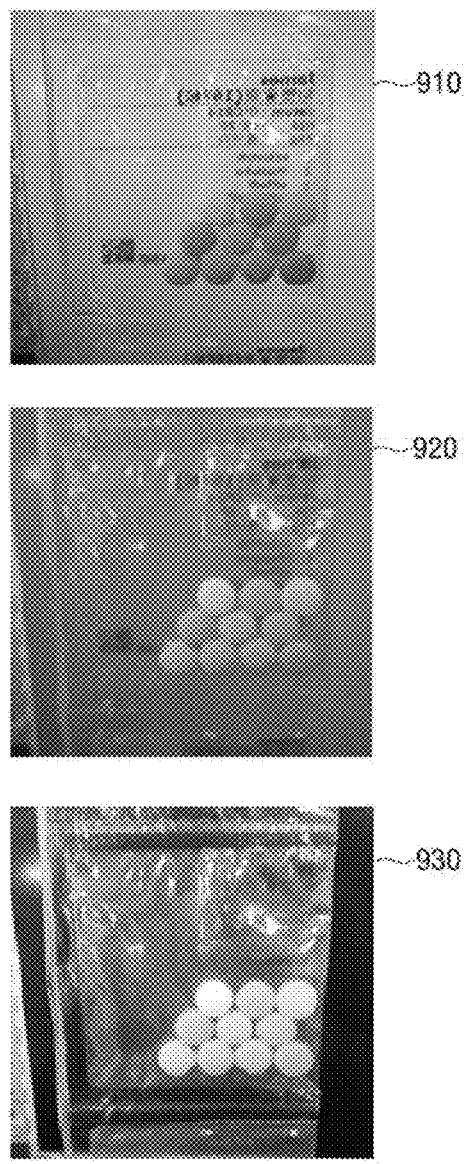
FIG. 7 shows images acquired by photographing a medicine packet plural times corresponding to lights of different colors in accordance with one embodiment of the present invention.

FIG. 7 shows images acquired by photographing a medicine packet plural times corresponding to lights of different colors in accordance with one embodiment of the present invention.

If the medicine packet is photographed on a white background, there is a possibility that white medicines may not be detected clearly.

If the medicine packet is photographed on a green background, there is a possibility that medicines having a color similar to green may not be detected clearly.

Further, since text is printed on the medicine packet, there is a possibility that medicines may not be detected clearly due to presence of the text.

Therefore, by photographing the medicine packet plural times using white light, green light and black light having the same color as the color (black) of the text, medicines having colors other than white may be clearly detected from an image 910 acquired by photographing the medicine packet under white light, medicines having colors other than colors similar to green may be clearly detected from an image 920 acquired by photographing the medicine packet under green light, and an image 930 from which the text is removed may be acquired by the photographing the medicine packet under black light, thereby allowing medicines to be clearly detected regardless of presence of the text.

Figure 8:
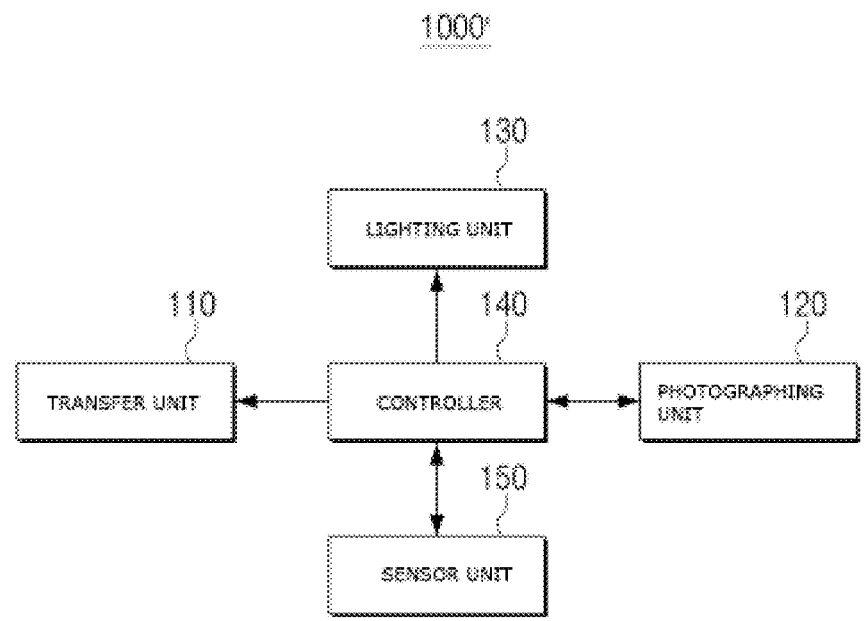
FIGS. 8 to 10 are block diagrams illustrating the configurations of medicine packet inspection apparatuses in accordance with other embodiments of the present invention.

FIG. 8 is a block diagram illustrating the configuration of a medicine packet inspection apparatus in accordance with a further embodiment of the present invention.

With reference to FIG. 8, a medicine packet inspection apparatus 100" may further include a sensor unit 150.

A transfer unit 110, a photographing unit 120, a lighting unit 130, and a controller 140 of the medicine packet inspection apparatus 100" in accordance with this embodiment may execute the same functions as those described in FIG. 1.

The sensor unit 150 may detect the color of text printed on the surface of a medicine packet and transmit the detected color to the controller 140.

In this case, the controller 140 may control the lighting unit 130 to emit light having the same color as the detected color of the text.

Figure 9:
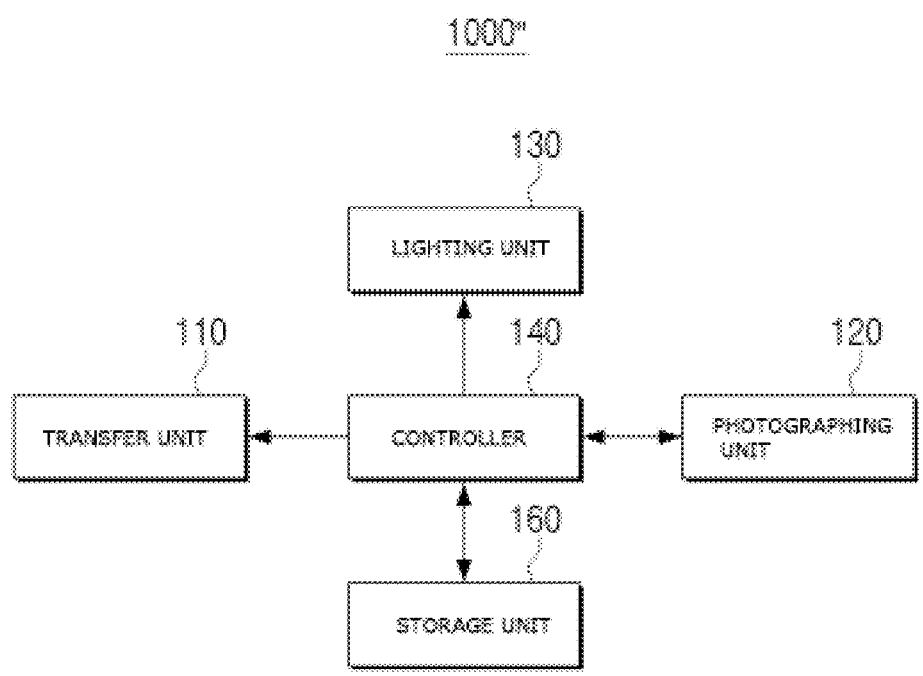

FIG. 9 is a block diagram illustrating the configuration of a medicine packet inspection apparatus in accordance with another embodiment of the present invention.

With reference to FIG. 9, a medicine packet inspection apparatus 100" may include a transfer unit 110, a photographing unit 120, a lighting unit 130, a controller 140 and a storage unit 160.

The transfer unit 110, the photographing unit 120, the lighting unit 130, and the controller 140 of the medicine packet inspection apparatus 100" in accordance with this embodiment may execute the same functions as those described in FIG. 1.

The controller 140 may deduce pattern information of respective medicines by receiving and analyzing images of the medicines which a medicine packet may contain.

In this case, the pattern information of medicines may include the sizes, amounts, shapes, colors, symbol marks, weights and thicknesses of the medicines.

The controller 140 may store the deduced pattern information of the respective medicines in the storage unit 160.

When the photographing unit 120 acquires images by photographing the medicine packet, the controller 140 may judge whether or not medicines matching medicine prescription information are packed in the medicine packet by analyzing patterns of the acquired images and comparing the analyzed patterns with the pattern information of medicines stored in the storage unit 160.

A barcode containing medicine prescription information may be printed on the medicine packet, and a barcode recognition unit (not shown) of the medicine packet inspection apparatus 100" may scan the barcode to detect the medicine prescription information. In this case, the controller 140 may store the detected medicine prescription information in the storage unit 160. Further, the controller 140 may judge whether or not medicines matching medicine prescription information are packed in the medicine packet by comparing medicines detected from a plurality of acquired images with the medicine prescription information stored in the storage unit 160.

Further, if medicine prescription information is input by a user, the medicine prescription information may be stored in the storage unit 160.

Figure 10:
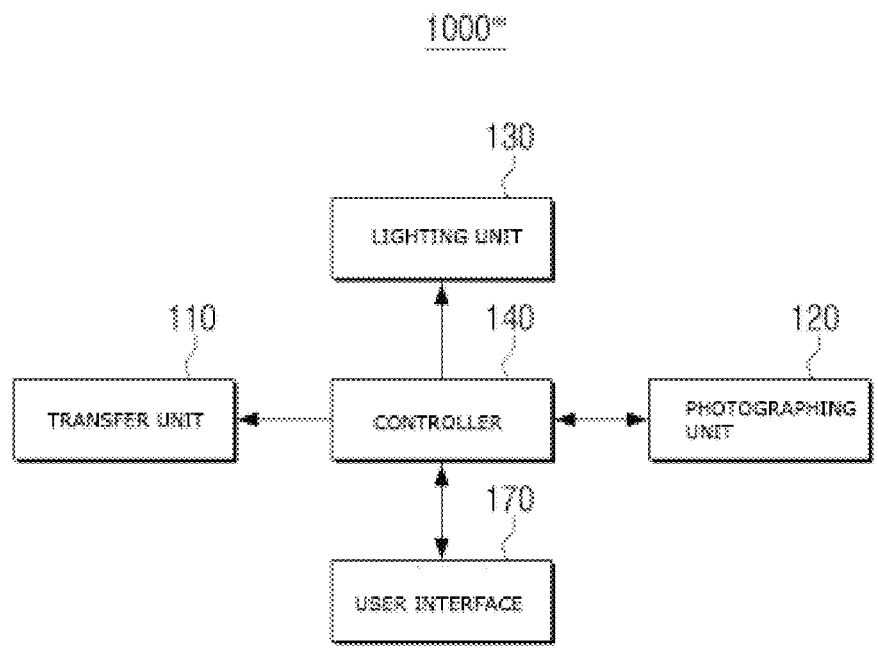

FIG. 10 is a block diagram illustrating the configuration of a medicine packet inspection apparatus in accordance with yet another embodiment of the present invention.

With reference to FIG. 10, a medicine packet inspection apparatus 100''' may include a transfer unit 110, a photographing unit 120, a lighting unit 130, a controller 140 and a user interface 170.

The transfer unit 110, the photographing unit 120, the lighting unit 130, and the controller 140 of the medicine packet inspection apparatus 100''' in accordance with this embodiment may execute the same functions as those described in FIG. 1.

The controller 140, if medicines detected from a plurality of images do not coincide with medicine prescription information, may inform the user of non-coincidence through the user interface 170.

Further, the user interface 170 may receive medicine prescription information from the user or receive information regarding the color of text printed on a medicine packet.

Further, the user interface 170 may provide information regarding the operating state of the medicine packet inspection apparatus 100''' to the user, and receive a user command to control operation of the medicine packet inspection apparatus 100'''.

Figure 11:
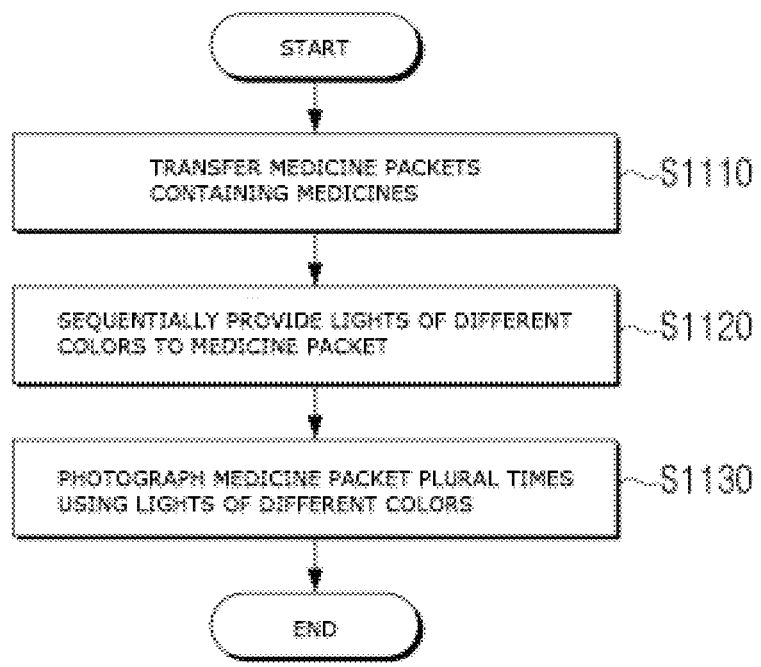
FIG. 11 is a flowchart illustrating a medicine packet inspection method in accordance with one embodiment of the present invention.

FIG. 11 is a flowchart illustrating a medicine packet inspection method in accordance with one embodiment of the present invention.

With reference to FIG. 11, medicine packets in which medicines are packed are transferred (Operation S1110). More specifically, in order to inspect the medicine packets in which medicines are packed, a medicine packet bundle in which the medicine packets are continuously connected may be transferred.

Thereafter, lights of different colors are sequentially provided to a medicine packet (Operation S1120). For example, lights of different colors may be sequentially provided to the medicine packet in a manner in which first light is provided, second light of a different color from the color of the first light is provided after provision of the first light, and third light of a different color from the colors of the first and second lights is provided after provision of the second light.

Thereafter, the medicine packet is photographed plural times corresponding to the lights of different colors (Operation S1130). More specifically, when a plurality of lights of different colors is sequentially provided to the medicine packet, the medicine packet may be photographed plural times corresponding to the lights of different colors.

Although all elements constituting the embodiments of the present invention are combined into one assembly, or are combined into one assembly and operated as the assembly, the disclosure of the present invention is not limited thereto. That is, one or more of all elements may be selected, combined into one assembly and operated as the assembly within the scope of the invention. Further, all elements may be respectively implemented as independent hardware, or some or all of the elements may be selectively combined and implemented by a computer program having a program module to execute the functions of the combined elements in one or plural hardware.

Codes and code segments constituting the computer program may be easily deduced by those skilled in the art of the present invention. Such a computer program may be stored in non-transitory computer readable media and read and executed by computers, thereby implementing the embodiments of the present invention.

Here, non-transitory computer readable media do not mean media which store data for a short period of time, such as a register, a cache, a memory, etc., but mean media which semipermanently store data and are readable by apparatuses. More specifically, the above-described programs may be stored in non-transitory computer readable media, such as a CD, a DVD, a hard disk, a Blu-ray disc, a USB, a memory card, a ROM, etc.

As apparent from the above description, a medicine packet inspection apparatus in accordance with one embodiment of the present invention sequentially provides lights of different colors to a medicine packet so as to photograph the medicine packet and may thus accurately recognize medicines in the medicine packet.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A medicine packet inspection apparatus, comprising:
a transfer unit configured to transfer medicine packets each containing medicines;
a photographing unit configured to photograph each medicine packet;
a lighting unit configured to provide light to the medicine packet to enhance a kind and number of the medicines; and
a controller configured to control the lighting unit to sequentially provide a first light having a color of white and at least one second light of a color different from the color of the first light and to control the photographing unit to photograph the medicine packet plural times corresponding to the first light and the at least one second light,
wherein the controller receives photographs acquired by the photographing unit to detect the kind and number of the medicines from the received photographs, and judge whether or not the medicines contained in the medicine packet match medicine prescription information by comparing the detected kind and number of the medicines in the photographs with the medicine prescription information.

2. The medicine packet inspection apparatus according to claim 1, wherein the lighting unit includes a first light emitting element to emit the first light and a second light emitting element to emit the at least one second light.

3. The medicine packet inspection apparatus according to claim 2, wherein the color of the at least one second light is contrasting to the white color of the first light.

4. The medicine packet inspection apparatus according to claim 1, wherein, when the controller determines that the medicines matching the medicine prescription information are not packed in the medicine packet, the controller:
controls the lighting unit to provide a light of a different color from the colors of the first light and the at least one second light; and
controls the photographing unit to additionally photograph the medicine packet corresponding to the light of the different color.

5. The medicine packet inspection apparatus according to claim 1, wherein the lighting unit is disposed opposite the photographing unit to provide the light to a rear surface of the medicine packet.

6. The medicine packet inspection apparatus according to claim 1, further comprising a subsidiary lighting unit configured to provide light to the medicine packet.

7. The medicine packet inspection apparatus according to claim 6, wherein the subsidiary lighting unit has a ring shape and is disposed on a side surface of the medicine packet.

8. The medicine packet inspection apparatus according to claim 6, further comprising a polarizing filter disposed between the medicine packet and at least one of the lighting unit and the subsidiary lighting unit.

9. A medicine packet inspection apparatus, comprising:
a transfer unit configured to transfer medicine packets each containing medicines;
a photographing unit configured to photograph each medicine packet;
a lighting unit configured to provide light to the medicine packet to enhance a kind and number of the medicines; and
a controller configured to control the lighting unit to sequentially provide lights of different colors to the medicine packet and to control the photographing unit to photograph the medicine packet plural times corresponding to the lights of different colors,
wherein the controller controls the lighting unit to sequentially provide a first light having a same color as a color of text printed on a surface of the medicine packet and at least one second light of a color different from the color of the first light,
wherein the controller receives photographs acquired by the photographing unit to detect the kind and number of the medicines from the received photographs, and judge whether or not the medicines contained in the medicine packet match medicine prescription information by comparing the detected kind and number of the medicines in the photographs with the medicine prescription information.

10. The medicine packet inspection apparatus according to claim 9, wherein the color of the first light is same as or complementary to a color of a medicine in the medicine packet.

11. A medicine packet inspection method, comprising:
transferring medicine packets each containing medicines;
sequentially providing a first light having a same color as a color of text printed on a surface of the medicine packet and at least one second light of a color different from the color of the first light to each medicine packet to enhance a kind and number of the medicines;
photographing the medicine packet plural times corresponding to the first light and the at least one second light to capture photographs;
receiving the photographs acquired by a photographing unit to a controller unit;
detecting the kind and number of the medicines from the received photographs; and
judging whether or not the medicines contained in the medicine packet match medicine prescription information by comparing the detected kind and number of the medicines in the photographs with the medicine prescription information.

12. The medicine packet inspection method according to claim 11, when the medicines matching the medicine prescription information are judged as not being packed in the medicine packet, further comprising:
   providing a light of a different color from the colors of the first light and the at least one second light; and
   additionally photographing the medicine packet corresponding to the light of the different color.

* * * * *